United States Patent
Gatineau et al.

(10) Patent No.: US 9,416,443 B2
(45) Date of Patent: Aug. 16, 2016

(54) METHOD FOR THE DEPOSITION OF A RUTHENIUM CONTAINING FILM USING ARENE DIAZADIENE RUTHENIUM(0) PRECURSORS

(71) Applicant: L'Air Liquide, Société Anonyme pour l'Etude et l'Exploitation des Procédés Georges Claude, Paris (FR)

(72) Inventors: Julien Gatineau, Tsuchiura (JP); Clément Lansalot-Matras, Seoul (KR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 187 days.

(21) Appl. No.: 14/377,294

(22) PCT Filed: Nov. 30, 2012

(86) PCT No.: PCT/IB2012/002554
§ 371 (c)(1),
(2) Date: Aug. 7, 2014

(87) PCT Pub. No.: WO2013/117955
PCT Pub. Date: Aug. 15, 2013

(65) Prior Publication Data
US 2015/0056384 A1    Feb. 26, 2015

Related U.S. Application Data

(60) Provisional application No. 61/595,788, filed on Feb. 7, 2012.

(51) Int. Cl.
*C23C 16/18* (2006.01)
*C07F 15/00* (2006.01)
(Continued)

(52) U.S. Cl.
CPC ............ *C23C 16/18* (2013.01); *C07F 15/0046* (2013.01); *C23C 16/50* (2013.01); *H01L 21/28556* (2013.01); *H01L 21/28562* (2013.01); *H01L 21/76841* (2013.01)

(58) Field of Classification Search
None
See application file for complete search history.

(56) References Cited

U.S. PATENT DOCUMENTS

2007/0072415 A1    3/2007 Suzuki

FOREIGN PATENT DOCUMENTS

| EP | 1 293 509 | 3/2003 | |
| KR | 20100060482 | * 11/2008 | ............ C07F 17/00 |

(Continued)

OTHER PUBLICATIONS

Choi, J. et al., "Composition and electrical properties of metallic Ru thin films deposited using Ru(C₆H₆) (C₆H₈) precursor," Japanese Journal of Applied Physics, 2002, vol. 41, Part 1, No. 11B, 6852-6856.

(Continued)

*Primary Examiner* — Mandy Louie
(74) *Attorney, Agent, or Firm* — Patricia E. McQueeney

(57) ABSTRACT

The invention concerns the use of ruthenium containing precursors having the formula (1) wherein R1, R2 . . . R10 are independently selected from H, C1-C4 linear, branched, or cyclic alkyl group, C1-C4 linear, branched, or cyclic alkylsilyl group (mono, bis, or trisalkyl), C1-C4 linear, branched, or cyclic alkylamino group, or a C1-C4 linear, branched, or cyclic fluoroalkyl group (totally fluorinated or not); for the deposition of a Ru containing film on a substrate.

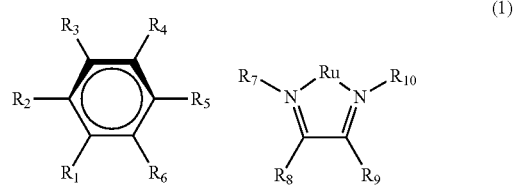

(1)

20 Claims, 1 Drawing Sheet

(51) Int. Cl.
*C23C 16/50* (2006.01)
*H01L 21/285* (2006.01)
*H01L 21/768* (2006.01)

(56) References Cited

FOREIGN PATENT DOCUMENTS

| WO | WO 2008 034468 | | 3/2008 | |
|---|---|---|---|---|
| WO | WO 2009 087609 | | 7/2009 | |
| WO | WO 2012 027357 | | 3/2012 | |
| WO | WO2012176988 | * | 12/2012 | ............... C23C 16/18 |
| WO | WO2014189340 | * | 11/2014 | ............... C23C 16/06 |

OTHER PUBLICATIONS

Kukli, K. et al., "Atomic layer deposition of Ru films from bis(2,5-dimethylpyrrolyl) ruthenium and oxygen," Thin Solid Film, 520 (2012) 756-2763.

Shibutami, T. et al., "A novel ruthenium precursor for MOCVD without seed ruthenium layer," Toshoh R&D Review, 47, 2003, 61-63.

Tom Dieck, D.H. et al., "Ruthenium complexes with diazadienes. 4. Arene diazadiene ruthenium(II) complexes [($\eta^6$-arene)(RN=CR'—CR'-NR)Ru(L)]$^{n+}$ ($n$=1, L=Cl, I, Alkyl; $n$==2, L=MeCN, $\eta^2$-$C_2H_4$) and arene diazadiene ruthynium(0)," Organometallics 1986, 5, 1449-1457.

International Search Report for corresponding PCT/IB2012/002554, Apr. 2, 2013.

* cited by examiner

METHOD FOR THE DEPOSITION OF A RUTHENIUM CONTAINING FILM USING ARENE DIAZADIENE RUTHENIUM(0) PRECURSORS

CROSS-REFERENCE TO RELATED APPLICATIONS

This application is a 371 of International PCT Application PCT/IB2012/002554, filed Nov. 30, 2012, which claims priority to U.S. provisional application No. 61/595,788, filed Feb. 7, 2012, the entire contents of each being incorporated herein by reference.

TECHNICAL FIELD

Disclosed are arene diazadiene Ruthenium(0) precursors used for the vapor deposition of ruthenium-containing films.

BACKGROUND

Ruthenium (Ru) is expected to be introduced in the industrial semiconductor manufacturing process for many applications in the coming years. This move towards the use of new materials for chip manufacturing is necessary to solve issues generated by the continuous scaling trend imposed to the industry. For the next generation nodes, Ru is considered as the best candidate for the electrode capacitor for FeRAM and DRAM applications. Ru has the required properties, such as high melting point, low resistivity, high oxidation resistance and adequate work function, making it a potential gate electrode material for CMOS transistor. Ru has advantages compared to iridium and platinum due to its lower resistivity and Ru ease of dry etching. Additionally, $RuO_2$ has a high conductivity so the formation of Ru oxide by diffusion of oxygen, that could come from ferroelectric films (PZT, SBT, BLT, . . . ), will have less impact on electrical properties than other metal oxides known to be more insulating.

Ru is also a promising BEOL process candidate as a liner material for copper. The poor wettability of Cu on currently used Ta/TaN barrier stack layers does not allow to directly deposit copper on such materials. The use of ruthenium between Ta/TaN and Cu is necessary to allow high quality thin copper gas-phase deposition with required adhesion strength to the Ru film prior to the ECD filling.

A large variety of Ru compounds are available and many have been studied as CVD precursors. However, the deposition process developed with these chemistries currently does not provide an answer the challenges of down-scaling imposed by the industry. Among other reasons, the need for an oxidant source to react with the ruthenium precursor (such as $Ru(EtCp)_2$, $Ru(EtCp)(Op)$, $Ru(Me2-pyrollyl)_2$) is considered as a source of damage to the under-laying nitride film, as the surface of such film will oxidize, generating less conductive interface. This will have a negative impact on the RC delay. Long incubation times are also frequently reported with the above mentioned precursors. This obviously generates control and production issues at the industrial stage (see T. Shibutami et al, Tosoh R&D Review, 47, 2003; K. Kukli et al., Thin Solid Film, 520 (2012) 2756-2763).

In order to avoid the use of an oxidant source, it is considered that ruthenium compounds having an oxidation state 0 should be used. With such compounds, pure ruthenium films can be used without co-reactant (see US20070072415, WO2008034468). A saturation regime typical of an Atomic Layer Deposition (ALD) mode may not be secured, but this is of relatively low concern given the relatively low aspect ratio patterns faced in BEOL application. However, a problem currently faced with such oxidation state 0 molecules is that they contain a carbonyl ligand, CO, which may damage the under-laying films.

Aside from the above mentioned precursors, some diazabutadiene based molecules have been developed. Diazabutadiene (DAD) ligands are α-diimine ligands that may be used under different oxidation states. The DAD ligand may be selected from one of three oxidation state forms, with each form determining the bonding mode between the center element (M) and the DAD ligands. As used herein, three different oxidation states of the ligand are described as i) neutral, ii) mono-anionic, and iii) dianionic. One of ordinary skill in the art will recognize that the location of the double bonds in the diazabutadiene ligand changes based upon the oxidation state of the ligand, as shown below:

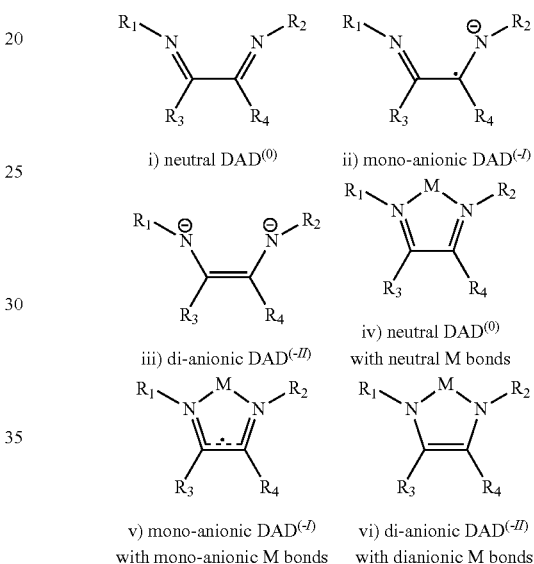

In Organometallics 1986, 5, 1449-1457, H.T. Dieck prepared the arene diazadiene ruthenium complex with the oxidation state 0. The complexes are prepared in two steps by preparing first the arene diazadiene chloro ruthenium (II) tetrafluoroborate complex followed by a reduction step with sodium naphtalene. When the complex is Ru(benzene) (dimethylglyoxal(bis-isopropylimine)) the final material has a melting point slightly above room temperature and can be purified by sublimation at 80° C. under vacuum.

A need remains for ruthenium containing precursors suitable for CVD or ALD using a ruthenium molecule that would have an oxidation state 0, and would not contain oxygen in its structure, and that such molecule allows the deposition of pure ruthenium films without any oxidant source with high enough uniformity onto the considered structures.

NOTATION AND NOMENCLATURE

Certain abbreviations, symbols, and terms are used throughout the following description and claims, and include:

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation "Me" refers to a methyl group; the abbreviation "Et" refers to an ethyl group; the abbreviation "Pr" refers to a n-propyl group; the abbreviation "iPr" refers to an isopropyl group; the abbreviation "Bu" refers to butyl (n-butyl), the abbreviation "tBu" refers to a tert-butyl; the abbreviation "sBu" refers to a sec-butyl, the abbreviation "ph" refers to a phenyl; the abbreviation "Cp" refers to cyclopentadienyl; the abbreviation "Cp*" refers to pentamethylcyclopentadienyl; the abbreviation "cod" refers to cyclooctadiene.

The standard abbreviations of the elements from the periodic table of elements are used herein. It should be understood that elements may be referred to by these abbreviations (e.g., Ni refers to nickel, Si refers to silicon, C refers to carbon, etc.).

As used herein, the abbreviation "DAD" refers to 1,4-diazabuta-1,3-diene ligand, an α-diimine which has general structure of $R_1$—N=$CR_3$—$CR_4$=N—$R_2$, wherein each $R_1$ to $R_4$ is independently selected from: H; C1-C6 linear, branched, or cyclic alkyl or aryl group; C1-C6 linear, branched, or cyclic alkylamino group such as NRR', where R and R' are independently selected from H or C1-C6 linear, branched, or cyclic alkyl or aryl group; C1-C6 linear, branched, or cyclic fluoroalkyl group (in which some or all of the substituents are F, i.e. partially or totally fluorinated); or an alkoxy substituent such as OR, where R is selected from H or a C1-C6 linear, branched, or cyclic alkyl or aryl group.

As used herein, the DAD ligand may be selected from one of three oxidation state forms, with each form determining the bonding mode between center element and DAD ligands. For a better understanding, the generic structures of the DAD ligands are represented below with three different oxidation state forms: i) neutral, ii) mono-anionic, and iii) dianionic. As described above, the term DAD refers to a generic structure that may be further substituted by substitution groups. One of ordinary skill in the art will recognize that the location of the double bonds in the diazabutadiene ligand changes based upon the oxidation state of the ligand, as shown below:

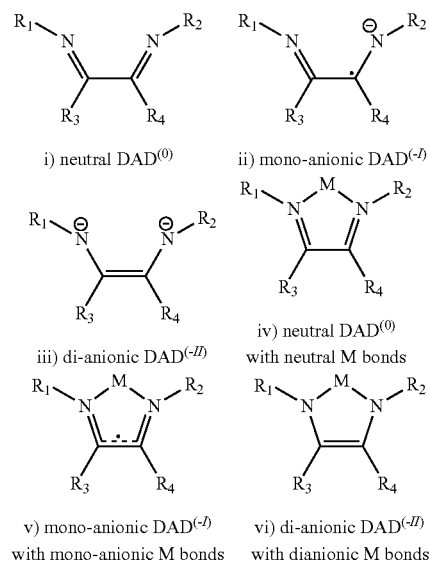

SUMMARY

Disclosed are processes for the deposition of ruthenium containing films on substrates. One or more ruthenium containing precursors are introduced into a reactor containing one or more substrates. At least part of the ruthenium containing precursor(s) is deposited onto the substrate(s) to form ruthenium containing film(s). The ruthenium containing precursor has the formula:

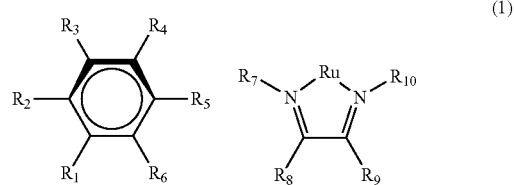

(1)

wherein $R_1$, $R_2$, $R_3$, $R_4$, $R_5$, $R_6$, $R_7$, $R_8$, $R_9$, and $R_{10}$ are independently selected from H; a C1-C4 linear, branched, or cyclic alkyl group; a C1-C4 linear, branched, or cyclic alkylsilyl group; a C1-C4 alkylamino group; or a C1-C4 linear, branched, or cyclic fluoroalkyl group. The disclosed processes may have one or more of the following aspects:

the ruthenium containing precursor being Ruthenium(benzene)(glyoxal(bis-methylimine));
the ruthenium containing precursor being Ruthenium(benzene)(glyoxal(bis-ethylimine));
the ruthenium containing precursor being Ruthenium(benzene)(glyoxal(bis-npropylimine));
the ruthenium containing precursor being Ruthenium(benzene)(glyoxal(bis-isopropylimine));
the ruthenium containing precursor being Ruthenium(benzene)(glyoxal(bis-nbutylimine));
the ruthenium containing precursor being Ruthenium(benzene)(glyoxal(bis-tertbutylimine));
the ruthenium containing precursor being Ruthenium(benzene)(glyoxal(bis-isobutylimine));
the ruthenium containing precursor being Ruthenium(benzene)(glyoxal(bis-trimethylsilylimine));
the ruthenium containing precursor being Ruthenium(benzene)(glyoxal(bis-trifluoromethylimine));
the ruthenium containing precursor being Ruthenium(benzene)(methylglyoxal(bis-methylimine));
the ruthenium containing precursor being Ruthenium(benzene)(methylglyoxal(bis-ethylimine));
the ruthenium containing precursor being Ruthenium(benzene)(methylglyoxal(bis-npropylimine));
the ruthenium containing precursor being Ruthenium(benzene)(methylglyoxal(bis-isopropylimine));
the ruthenium containing precursor being Ruthenium(benzene)(methylglyoxal(bis-nbutylimine));
the ruthenium containing precursor being Ruthenium(benzene)(methylglyoxal(bis-tertbutylimine));
the ruthenium containing precursor being Ruthenium(benzene)(methylglyoxal(bis-isobutylimine));
the ruthenium containing precursor being Ruthenium(benzene)(methylgiyoxal(bis-trimethylsilylimine));
the ruthenium containing precursor being Ruthenium(benzene)(methylglyoxal(bis-trifluoromethylimine));
the ruthenium containing precursor being Ruthenium(benzene)(dimethylglyoxal(bis-methylimine));
the ruthenium containing precursor being Ruthenium(benzene)(dimethylglyoxal(bis-ethylimine));

the ruthenium containing precursor being Ruthenium(benzene)(dimethylglyoxal(bis-npropylimine));
the ruthenium containing precursor being Ruthenium(benzene)(dimethylglyoxal(bis-isopropylimine));
the ruthenium containing precursor being Ruthenium(benzene)(dimethylglyoxal(bis-nbutylimine));
the ruthenium containing precursor being Ruthenium(benzene)(dimethylglyoxal(bis-tertbutylimine));
the ruthenium containing precursor being Ruthenium(benzene)(dimethylglyoxal(bis-isobutylimine));
the ruthenium containing precursor being Ruthenium(benzene)(dimethylglyoxal(bis-trimethylsilylimine));
the ruthenium containing precursor being Ruthenium(benzene)(dimethylglyoxal(bis-trifluoromethylimine));
the ruthenium containing precursor being Ruthenium(m-ethylbenzene)(glyoxal(bis-methylimine));
the ruthenium containing precursor being Ruthenium(m-ethylbenzene)(glyoxal(bis-ethylimine));
the ruthenium containing precursor being Ruthenium(m-ethylbenzene)(glyoxal(bis-npropylimine));
the ruthenium containing precursor being Ruthenium(m-ethylbenzene)(glyoxal(bis-isopropylimine));
the ruthenium containing precursor being Ruthenium(m-ethylbenzene)(glyoxal(bis-nbutylimine));
the ruthenium containing precursor being Ruthenium(m-ethylbenzene)(glyoxal(bis-tertbutylimine));
the ruthenium containing precursor being Ruthenium(m-ethylbenzene)(glyoxal(bis-isobutylimine));
the ruthenium containing precursor being Ruthenium(m-ethylbenzene)(glyoxal(bis-trimethylsilylimine));
the ruthenium containing precursor being Ruthenium(m-ethylbenzene)(glyoxal(bis-trifluoromethylimine));
the ruthenium containing precursor being Ruthenium(m-ethylbenzene)(methylglyoxal(bis-methylimine));
the ruthenium containing precursor being Ruthenium(m-ethylbenzene)(methylglyoxal(bis-ethylimine));
the ruthenium containing precursor being Ruthenium(m-ethylbenzene)(methylglyoxal(bis-npropylimine));
the ruthenium containing precursor being Ruthenium(m-ethylbenzene)(methylglyoxal(bis-isopropylimine));
the ruthenium containing precursor being Ruthenium(m-ethylbenzene)(methylglyoxal(bis-nbutylimine));
the ruthenium containing precursor being Ruthenium(m-ethylbenzene)(methylglyoxal(bis-tertbutylimine));
the ruthenium containing precursor being Ruthenium(m-ethylbenzene)(methylglyoxal(bis-isobutylimine));
the ruthenium containing precursor being Ruthenium(m-ethylbenzene)(methylglyoxal(bis-trimethylsilylimine));
the ruthenium containing precursor being Ruthenium(m-ethylbenzene)(methylglyoxal(bis-trifluoromethylimine));
the ruthenium containing precursor being Ruthenium(m-ethylbenzene)(dimethylglyoxal(bis-methylimine));
the ruthenium containing precursor being Ruthenium(m-ethylbenzene)(dimethylglyoxal(bis-ethylimine));
the ruthenium containing precursor being Ruthenium(m-ethylbenzene)(dimethylglyoxal(bis-npropylimine));
the ruthenium containing precursor being Ruthenium(m-ethylbenzene)(dimethylglyoxal(bis-isopropylimine));
the ruthenium containing precursor being Ruthenium(m-ethylbenzene)(dimethylglyoxal(bis-nbutylimine));
the ruthenium containing precursor being Ruthenium(m-ethylbenzene)(dimethylglyoxal(bis-tertbutylimine));
the ruthenium containing precursor being Ruthenium(m-ethylbenzene)(dimethylglyoxal(bis-isobutylimine));
the ruthenium containing precursor being Ruthenium(m-ethylbenzene)(dimethylglyoxal(bis-trimethylsilylimine));
the ruthenium containing precursor being Ruthenium(m-ethylbenzene)(dimethylglyoxal(bis-trifluoromethylimine));
the ruthenium containing film being Ru;
annealing the ruthenium containing film;
maintaining the reactor at a temperature between about 25° C. to about 500° C.;
maintaining the reactor at a temperature between about 50° C. and about 350° C.;
maintaining the reactor at a pressure between about 1 Pa and about $10^5$ Pa; maintaining the reactor at a pressure between about 10 Pa and about $10^3$ Pa;
introducing at least one reactant into the reactor;
introducing the ruthenium-containing precursor and the reactant into the chamber substantially simultaneously;
configuring the chamber for chemical vapor deposition;
configuring the chamber for plasma enhanced chemical vapor deposition;
introducing the ruthenium-containing precursor and the reactant into the chamber sequentially;
configuring the chamber for atomic layer deposition;
configuring the chamber for plasma enhanced atomic layer deposition;
configuring the chamber for spatial atomic layer deposition;
the reactant being selected from the group consisting of $H_2$, $NH_3$, $SiH_4$, $Si_2H_6$, $Si_3H_8$, $(CH_3)_2SiH_2$, $(C_2H_5)_2SiH_2$, $(CH_3)SiH_3$, $(C_2H_5)SiH_3$, phenyl silane, $N_2H_4$, $N(SiH_3)_3$, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$, $(CH_3)HNNH_2$, $(CH_3)_2NNH_2$, phenyl hydrazine, N-containing molecules, $B_2H_6$, 9-borabicyclo[3,3,1]nonane, dihydrobenzenfuran, pyrazoline, trimethylaluminium, dimethylzinc, diethylzinc, radical species thereof, and mixtures thereof; and
the reactant being selected from the group consisting of: $O_2$, $O_3$, $H_2O$, $H_2O_2$, oxygen containing radicals such as O. or OH., NO, $NO_2$, carboxylic acids, formic acid, acetic acid, propionic acid, and mixtures thereof.

BRIEF DESCRIPTION OF THE FIGURES

For a further understanding of the nature and objects of the present invention, reference should be made to the following detailed description, taken in conjunction with the accompanying figure wherein.

DETAILED DESCRIPTION OF PREFERRED EMBODIMENTS

Figure 1:
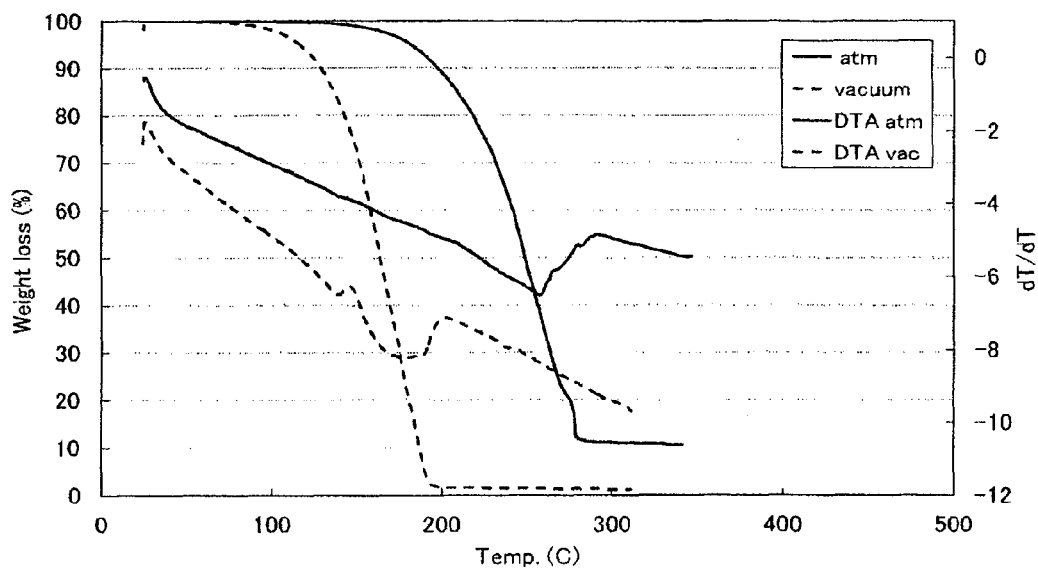
FIG. 1 is a ThermoGravimetric Analysis (TGA) and Differential Thermal Analysis (DTA) graph demonstrating the percentage of weight loss (TGA) or the differential temperature (DTA) with increasing temperature of Ru(benzene)(dimethylglyoxal bis-isopropylimine)

Disclosed are methods for forming ruthenium-containing layers on substrates using a vapor deposition process using ruthenium-containing precursors having the formula:

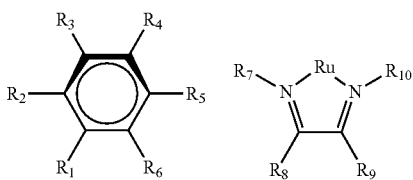

wherein $R_1$, $R_2$, $R_3$, $R_4$, $R_5$, $R_6$, $R_7$, $R_8$, $R_9$, $R_{10}$ is independently selected from H; a C1-C4 linear, branched, or cyclic alkyl group; a C1-C4 linear, branched, or cyclic alkylsilyl group (mono, bis, or trisalkyl); a C1-C4 linear, branched, or cyclic alkylamino group; or a C1-C4 linear, branched, or cyclic fluoroalkyl group (totally fluorinated or not).

Preferably, the ruthenium precursor is selected from, but without limitation, the group consisting of:
Ruthenium(benzene)(glyoxal(bis-methylimine))
Ruthenium(benzene)(glyoxal(bis-ethylimine))
Ruthenium(benzene)(glyoxal(bis-npropylimine))
Ruthenium(benzene)(glyoxal(bis-isopropylimine))
Ruthenium(benzene)(glyoxal(bis-nbutylimine))
Ruthenium(benzene)(glyoxal(bis-tertbutylimine))
Ruthenium(benzene)(glyoxal(bis-isobutylimine))
Ruthenium(benzene)(glyoxal(bis-trimethylsilylimine))
Ruthenium(benzene)(glyoxal(bis-trifluoromethylimine))
Ruthenium(benzene)(methylglyoxal(bis-methylimine))
Ruthenium(benzene)(methylglyoxal(bis-ethylimine))
Ruthenium(benzene)(methylglyoxal(bis-npropylimine))
Ruthenium(benzene)(methylglyoxal(bis-isopropylimine))
Ruthenium(benzene)(methylglyoxal(bis-nbutylimine))
Ruthenium(benzene)(methylglyoxal(bis-tertbutylimine))
Ruthenium(benzene)(methylglyoxal(bis-isobutylimine))
Ruthenium(benzene)(methylglyoxal(bis-trimethylsilylimine))
Ruthenium(benzene)(methylglyoxal(bis-trifluoromethylimine))
Ruthenium(benzene)(dimethylglyoxal(bis-methylimine))
Ruthenium(benzene)(dimethylglyoxal(bis-ethylimine))
Ruthenium(benzene)(dimethylglyoxal(bis-npropylimine))
Ruthenium(benzene)(dimethylglyoxal(bis-isopropylimine))
Ruthenium(benzene)(dimethylglyoxal(bis-nbutylimine))
Ruthenium(benzene)(dimethylglyoxal(bis-tertbutylimine))
Ruthenium(benzene)(dimethylglyoxal(bis-isobutylimine))
Ruthenium(benzene)(dimethylglyoxal(bis-trimethylsilylimine))
Ruthenium(benzene)(dimethylglyoxal(bis-trifluoromethylimine))
Ruthenium(methylbenzene)(glyoxal(bis-methylimine))
Ruthenium(methylbenzene)(glyoxal(bis-ethylimine))
Ruthenium(methylbenzene)(glyoxal(bis-npropylimine))
Ruthenium(methylbenzene)(glyoxal(bis-isopropylimine))
Ruthenium(methylbenzene)(glyoxal(bis-nbutylimine))
Ruthenium(methylbenzene)(glyoxal(bis-tertbutylimine))
Ruthenium(methylbenzene)(glyoxal(bis-isobutylimine))
Ruthenium(methylbenzene)(glyoxal(bis-trimethylsilylimine))
Ruthenium(methylbenzene)(glyoxal(bis-trifluoromethylimine))
Ruthenium(methylbenzene)(methylglyoxal(bis-methylimine))
Ruthenium(methylbenzene)(methylglyoxal(bis-ethylimine))
Ruthenium(methylbenzene)(methylglyoxal(bis-npropylimine))
Ruthenium(methylbenzene)(methylglyoxal(bis-isopropylimine))
Ruthenium(methylbenzene)(methylglyoxal(bis-nbutylimine))
Ruthenium(methylbenzene)(methylglyoxal(bis-tertbutylimine))
Ruthenium(methylbenzene)(methylglyoxal(bis-isobutylimine))
Ruthenium(methylbenzene)(methylglyoxal(bis-trimethylsilylimine))
Ruthenium(methylbenzene)(methylglyoxal(bis-trifluoromethylimine))
Ruthenium(methylbenzene)(dimethylglyoxal(bis-methylimine))
Ruthenium(methylbenzene)(dimethylglyoxal(bis-ethylimine))
Ruthenium(methylbenzene)(dimethylglyoxal(bis-npropylimine))
Ruthenium(methylbenzene)(dimethylglyoxal(bis-isopropylimine))
Ruthenium(methylbenzene)(dimethylglyoxal(bis-nbutylimine))
Ruthenium(methylbenzene)(dimethylglyoxal(bis-tertbutylimine))
Ruthenium(methylbenzene)(dimethylglyoxal(bis-isobutylimine))
Ruthenium(methylbenzene)(dimethylglyoxal(bis-trimethylsilylimine))
Ruthenium(methylbenzene)(dimethylglyoxal(bis-trifluoromethylimine))

Preferably, the ruthenium-containing precursor is Ruthenium(benzene)(dimethylglyoxal(bis-isopropylimine)) (with $R_1$ to $R_6$=H; $R_7$, $R_{10}$=iPr; and $R_8$, $R_9$=Me in the formula above) or Ru(benzene)(glyoxalbis-isopropylimine) (with $R_1$ to $R_6$=H; $R_7$, $R_{10}$=iPr; and $R_8$, $R_9$=H in the formula above) due to the excellent vaporization results in vacuum thermogravimetric analysis, leaving a small amount of final residue.

The disclosed ruthenium-containing precursors may be synthesized in two steps by preparing first the arene diazadiene chloro ruthenium (II) tetrafluoroborate complex followed by a reduction step with sodium naphtalene. Exemplary synthesis methods containing further details are provided in the Examples that follow.

The method may be useful in the manufacture of semiconductor, photovoltaic, LCD-TFT, or flat panel type devices. The disclosed ruthenium-containing precursors may be used to deposit thin ruthenium-containing films using any deposition methods known to those of skill in the art. Examples of suitable deposition methods include without limitation, conventional chemical vapor deposition (CVD), plasma enhanced chemical vapor deposition (PECVD), low pressure chemical vapor deposition (LPCVD), plasma enhanced chemical vapor depositions (PECVD), atomic layer deposition (ALD), pulsed chemical vapor deposition (PCVD), plasma enhanced atomic layer deposition (PEALD), spatial ALD, or combinations thereof.

The disclosed ruthenium-containing precursors may be supplied either in neat form or in a blend with a suitable solvent, such as ethyl benzene, xylene, mesitylene, decane, dodecane. The disclosed precursors may be present in varying concentrations in the solvent.

One or more of the neat or blended ruthenium-containing precursors are introduced into a reactor in vapor form by conventional means, such as tubing and/or flow meters. The vapor form of the precursor may be produced by vaporizing the neat or blended precursor solution through a conventional vaporization step such as direct vaporization, distillation, by bubbling, or by using a sublimator such as the one disclosed in PCT Publication WO2009/087609 to Xu et al. The neat or blended precursor may be fed in liquid state to a vaporizer where it is vaporized before it is introduced into the reactor. Alternatively, the neat or blended precursor may be vaporized by passing a carrier gas into a container containing the precursor or by bubbling the carrier gas into the precursor. The carrier gas may include, but is not limited to, Ar, He, $N_2$, and mixtures thereof. Bubbling with a carrier gas may also remove any dissolved oxygen present in the neat or blended precursor solution. The carrier gas and precursor are then introduced into the reactor as a vapor.

If necessary, the container of disclosed precursor may be heated to a temperature that permits the precursor to be in its liquid phase and to have a sufficient vapor pressure. The container may be maintained at temperatures in the range of, for example, approximately 0° C. to approximately 150° C. Those skilled in the art recognize that the temperature of the container may be adjusted in a known manner to control the amount of precursor vaporized.

The reactor may be any enclosure or chamber within a device in which deposition methods take place such as without limitation, a parallel-plate type reactor, a cold-wall type reactor, a hot-wall type reactor, a single-wafer reactor, a multi-wafer reactor, or other types of deposition systems under conditions suitable to cause the precursors to react and form the layers.

Generally, the reactor contains one or more substrates onto which the thin films will be deposited. The one or more substrates may be any suitable substrate used in semiconductor, photovoltaic, flat panel, or LCD-TFT device manufacturing. Examples of suitable substrates include without limitation, silicon substrates, silica substrates, silicon nitride substrates, silicon oxy nitride substrates, tungsten substrates, tantalum substrates, tantalum nitride substrates, titanium substrates, titanium nitride substrates, zirconium substrates, zirconium nitride substrates, or combinations thereof. Additionally, substrates comprising tantalum or tantalum nitride (or other refractory metals or refractory metal nitrides) may be used. The substrate may also have one or more layers of differing materials already deposited upon it from a previous manufacturing step.

The temperature and the pressure within the reactor are held at conditions suitable for ALD or CVD depositions. In other words, after introduction of the vaporized precursor into the chamber, conditions within the chamber are such that at least part of the vaporized precursor is deposited onto the substrate to form a ruthenium-containing film. For instance, the pressure in the reactor may be held between about 1 Pa and about $10^5$ Pa, more preferably between about 25 Pa and about $10^3$ Pa, as required per the deposition parameters. Likewise, the temperature in the reactor may be held between about 25° C. and about 500° C., preferably between about 100° C. and about 350° C.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 25° C. to approximately 500° C. When a plasma deposition process is utilized, the deposition temperature may range from approximately 25° C. to approximately 350° C. Alternatively, when a thermal process is performed, the deposition temperature may range from approximately 50° C. to approximately 500° C.

In addition to the disclosed precursor, a reactant may also be introduced into the reactor. The reactant may be an oxidizing gas such as one of $O_2$, $O_3$, $H_2O$, $H_2O_2$, oxygen containing radicals such as O. or OH., NO, $NO_2$, carboxylic acids, formic acid, acetic acid, propionic acid, and mixtures thereof. Preferably, the oxidizing gas is selected from the group consisting of $O_2$, $O_3$, $H_2O$, $H_2O_2$, oxygen containing radicals thereof such as O. or OH., and mixtures thereof. Alternatively, the reactant may be a reducing gas such as one of $H_2$, $NH_3$, $SiH_4$, $Si_2H_6$, $Si_3H_8$, $(CH_3)_2SiH_2$, $(C_2H_5)_2SiH_2$, $(CH_3)SiH_3$, $(C_2H_5)SiH_3$, phenyl silane, $N_2H_4$, $N(SiH_3)_3$, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$, $(CH_3)HNNH_2$, $(CH_3)_2NNH_2$, phenyl hydrazine, N-containing molecules, $B_2H_6$, 9-borabicyclo [3,3,1]nonane, dihydrobenzenfuran, pyrazoline, trimethylaluminium, dimethylzinc, diethylzinc, radical species thereof, and mixtures thereof. Preferably, the reducing as is $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, or mixtures thereof.

The reactant may be treated by a plasma, in order to decompose the reactant into its radical form. $N_2$ may also be utilized as a reducing gas when treated with plasma. For instance, the plasma may be generated with a power ranging from about 50 W to about 500 W, preferably from about 100 W to about 200 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

The vapor deposition conditions within the chamber allow the disclosed precursor and the reactant to react and form a ruthenium-containing film on the substrate. In some embodiments, Applicants believe that plasma-treating the reactant may provide the reactant with the energy needed to react with the disclosed precursor.

Depending on what type of film is desired to be deposited, a second precursor may be introduced into the reactor. The second precursor may be used to provide additional elements to the ruthenium-containing film. The additional elements may include copper, phosphorus, manganese, titanium, tantalum, bismuth, zirconium, hafnium, lead, niobium, magnesium, aluminum, iridium, platinum, or mixtures of these. When a second precursor is utilized, the resultant film deposited on the substrate may contain ruthenium in combination with at least one additional element.

The ruthenium-containing precursors and reactants may be introduced into the reactor either simultaneously (chemical vapor deposition), sequentially (atomic layer deposition) or different combinations thereof. The reactor may be purged with an inert gas between the introduction of the precursor and the introduction of the reactant. Alternatively, the reactant and the precursor may be mixed together to form a reactant/precursor mixture, and then introduced to the reactor in mixture form. Another example is to introduce the reactant continuously and to introduce the at least one ruthenium-containing precursor by pulse (pulsed chemical vapor deposition).

The vaporized precursor and the reactant may be pulsed sequentially or simultaneously (e.g. pulsed CVD) into the reactor. Each pulse of precursor may last for a time period ranging from about 0.01 seconds to about 10 seconds, alternatively from about 0.05 seconds to about 3 seconds, alternatively from about 0.1 seconds to about 2 seconds. In another embodiment, the reactant may also be pulsed into the reactor. In such embodiments, the pulse of each gas may last for a time period ranging from about 0.01 seconds to about 10 seconds, alternatively from about 0.05 seconds to about 3 seconds, alternatively from about 0.1 seconds to about 2 seconds. In another alternative, the vaporized precursor and one or more reactants may be simultaneously sprayed from a shower head under which a susceptor holding several wafers is spun (spatial ALD).

Depending on the particular process parameters, deposition may take place for a varying length of time. Generally, deposition may be allowed to continue as long as desired or necessary to produce a film with the necessary properties. Typical film thicknesses may vary from several angstroms to several hundreds of microns, depending on the specific deposition process. The deposition process may also be performed as many times as necessary to obtain the desired film.

In one non-limiting exemplary CVD type process, the vapor phase of the disclosed ruthenium-containing precursor and a reactant are simultaneously introduced into the reactor. The two react to form the resulting ruthenium-containing thin film. When the reactant in this exemplary CVD process is treated with a plasma, the exemplary CVD process becomes an exemplary PECVD process. The reactant may be treated with plasma prior or subsequent to introduction into the chamber.

In one non-limiting exemplary ALD type process, the vapor phase of the disclosed ruthenium-containing precursor is introduced into the reactor, where it is contacted with a suitable substrate. Excess precursor may then be removed from the reactor by purging and/or evacuating the reactor. A reducing gas (for example, $H_2$) is introduced into the reactor where it reacts with the absorbed precursor in a self-limiting manner. Any excess reducing gas is removed from the reactor by purging and/or evacuating the reactor. If the desired film is a ruthenium film, this two-step process may provide the desired film thickness or may be repeated until a film having the necessary thickness has been obtained.

Alternatively, if the desired film contains ruthenium and a second element, the two-step process above may be followed by introduction of the vapor of a second precursor into the reactor. The second precursor will be selected based on the nature of the ruthenium film being deposited. After introduction into the reactor, the second precursor is contacted with the substrate. Any excess second precursor is removed from the reactor by purging and/or evacuating the reactor. Once again, a reducing gas may be introduced into the reactor to react with the second precursor. Excess reducing gas is removed from the reactor by purging and/or evacuating the reactor. If a desired film thickness has been achieved, the process may be terminated. However, if a thicker film is desired, the entire four-step process may be repeated. By alternating the provision of the ruthenium-containing precursor, second precursor, and reactant, a film of desired composition and thickness can be deposited.

When the reactant in this exemplary ALD process is treated with a plasma, the exemplary ALD process becomes an exemplary PEALD process. The reactant may be treated with plasma prior or subsequent to introduction into the chamber.

The ruthenium-containing films resulting from the processes discussed above may include a pure ruthenium (Ru) or ruthenium oxide ($Ru_nO_m$) film wherein m and n are integers which inclusively range from 1 to 6. One of ordinary skill in the art will recognize that by judicial selection of the appropriate disclosed precursor, optional second precursors, and reactant species, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the ruthenium-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 400° C. for 3600 seconds or less under a H-containing atmosphere. The resulting film may contain fewer impurities and therefore may have an improved density resulting in improved leakage current. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the ruthenium-containing film. This in turn tends to improve the resistivity of the film.

EXAMPLES

The following examples illustrate experiments performed in conjunction with the disclosure herein. The examples are not intended to be all inclusive and are not intended to limit the scope of disclosure described herein.

Example 1

Ru(benzene)(dimethylglyoxalbis-isopropylimine) was prepared according to the procedure described in Organometallics 1986, 5, 1449-1457 as a red liquid which melting point is slightly above room temperature.

The red liquid left a <11% residual mass during TGA analysis measured at a temperature rising rate of 10° C./min in an atmosphere which flows nitrogen at 220 mL/min. In vacuum condition (20 mBar) the red liquid left a <1% residual mass. These results are depicted in FIG. 1, which is a TGA graph demonstrating the percentage of weight loss with temperature change. Vapor pressure of the precursor was assessed as 1 Torr at 140° C.

Example 2

Ru(benzene)(glyoxalbis-isopropylimine) was prepared according to the procedure described in Organometallics 1986, 5, 1449-1457 as a red solid which melting point is 96° C.

Figure 2:
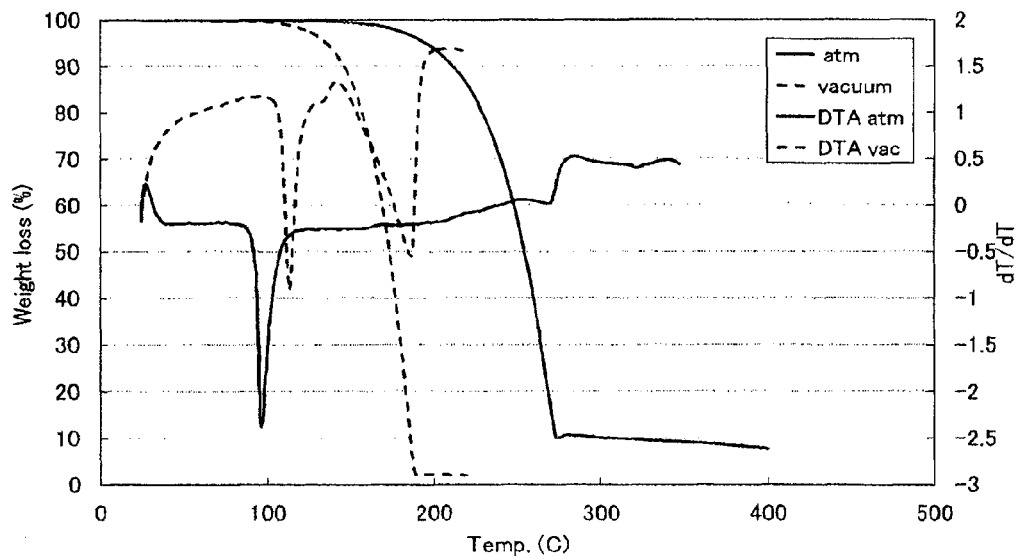
FIG. 2 is a TGA and DTA graph demonstrating the percentage of weight loss or the differential temperature with increasing temperature of Ru(benzene)(glyoxalbis-isopropylimine).

The red solid left a 8% residual mass during TGA analysis measured at a temperature rising rate of 10° C./min in an atmosphere which flows nitrogen at 220 mL/min. In vacuum condition (20 mBar) the red liquid left a <2% residual mass. These results are depicted in FIG. 2, which is a TGA graph demonstrating the percentage of weight loss with temperature change. Vapor pressure of the precursor was assessed as 1 Torr at 145° C.

Prophetic Example 3

Ru(benzene)(glyoxalbis-isopropylimine) will be prepared as mentioned in Example 2. Ru(benzene)(glyoxalbis-isopropylimine) will be stored in a container (bubbler or canister for instance) within inert atmosphere. The vapors of the precursors will be introduced in a reaction furnace where some substrates are placed. A flow of hydrogen, $H_2$, will also be allowed to enter the reaction furnace, simultaneously to the ruthenium precursor (CVD) or in separated and repeated fashion (ALD). The vapors of the precursor will be provided by a bubbling method. The container will be heated at 80 C to control the flow of precursor to be provided to the reaction chamber. When the precursor and hydrogen react together in the reaction furnace at 250° C., highly uniform ruthenium containing films will be obtained even for very thin films of <5 nm (no island type growth). Resistivity of these thin ruthenium-containing films will be <50 μΩ·cm.

Prophetic Example 4

$RuO_2$ films will be obtained in a similar fashion to Prophetic Example 3, but oxygen will be used instead of hydrogen. When the precursor and oxygen react together in the reaction furnace at 250° C., highly uniform ruthenium oxide containing films will be obtained even for very thin films of <5 nm (no island type growth). Resistivity of these thin ruthenium-containing films will be <100 μΩ·cm.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:

1. A process for the deposition of a ruthenium containing film on a substrate, comprising the steps of:
   a) introducing at least one ruthenium containing precursor into a reactor containing one or more substrates, wherein the at least one ruthenium containing precursor has the formula:

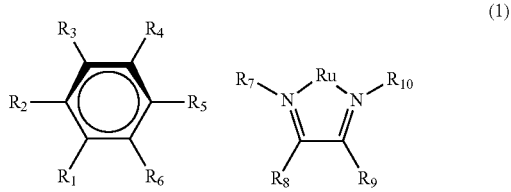

(1)

wherein
   $R_1$, $R_2$, $R_3$, $R_4$, $R_5$, $R_6$, $R_7$, $R_8$, $R_9$, and $R_{10}$ are independently selected from H; a C1-C4 linear, branched, or cyclic alkyl group; a C1-C4 linear, branched, or cyclic alkylsilyl group; a C1-C4 alkylamino group; or a C1-C4 linear, branched, or cyclic fluoroalkyl group; and b) Depositing at least part of the ruthenium containing precursor onto the at least one substrate to form a ruthenium containing film.

2. The process of claim 1, wherein the ruthenium containing precursor is selected from the group consisting of:
   Ruthenium(benzene)(glyoxal(bis-methylimine));
   Ruthenium(benzene)(glyoxal(bis-ethylimine));
   Ruthenium(benzene)(glyoxal(bis-npropylimine));
   Ruthenium(benzene)(glyoxal(bis-isopropylimine));
   Ruthenium(benzene)(glyoxal(bis-nbutylimine));
   Ruthenium(benzene)(glyoxal(bis-tertbutylimine));
   Ruthenium(benzene)(glyoxal(bis-isobutylimine));
   Ruthenium(benzene)(glyoxal(bis-trimethylsilylimine));
   Ruthenium(benzene)(glyoxal(bis-trifluoromethylimine));
   Ruthenium(benzene)(methylglyoxal(bis-methylimine));
   Ruthenium(benzene)(methylglyoxal(bis-ethylimine));
   Ruthenium(benzene)(methylglyoxal(bis-npropylimine));
   Ruthenium(benzene)(methylglyoxal(bis-isopropylimine));
   Ruthenium(benzene)(methylglyoxal(bis-nbutylimine));
   Ruthenium(benzene)(methylglyoxal(bis-tertbutylimine));
   Ruthenium(benzene)(methylglyoxal(bis-isobutylimine));
   Ruthenium(benzene)(methylglyoxal(bis-trimethylsilylimine));
   Ruthenium(benzene)(methylglyoxal(bis-trifluoromethylimine));
   Ruthenium(benzene)(dimethylglyoxal(bis-methylimine));
   Ruthenium(benzene)(dimethylglyoxal(bis-ethylimine));
   Ruthenium(benzene)(dimethylglyoxal(bis-npropylimine));
   Ruthenium(benzene)(dimethylglyoxal(bis-isopropylimine));
   Ruthenium(benzene)(dimethylglyoxal(bis-nbutylimine));
   Ruthenium(benzene)(dimethylglyoxal(bis-tertbutylimine));
   Ruthenium(benzene)(dimethylglyoxal(bis-isobutylimine));
   Ruthenium(benzene)(dimethylglyoxal(bis-trimethylsilylimine));
   Ruthenium(benzene)(dimethylglyoxal(bis-trifluoromethylimine));
   Ruthenium(methylbenzene)(glyoxal(bis-methylimine));
   Ruthenium(methylbenzene)(glyoxal(bis-ethylimine));
   Ruthenium(methylbenzene)(glyoxal(bis-npropylimine));
   Ruthenium(methylbenzene)(glyoxal(bis-isopropylimine));
   Ruthenium(methylbenzene)(glyoxal(bis-nbutylimine));
   Ruthenium(methylbenzene)(glyoxal(bis-tertbutylimine));
   Ruthenium(methylbenzene)(glyoxal(bis-isobutylimine));
   Ruthenium(methylbenzene)(glyoxal(bis-trimethylsilylimine));
   Ruthenium(methylbenzene)(glyoxal(bis-trifluoromethylimine));
   Ruthenium(methylbenzene)(methylglyoxal(bis-methylimine));
   Ruthenium(methylbenzene)(methylglyoxal(bis-ethylimine));
   Ruthenium(methylbenzene)(methylglyoxal(bis-npropylimine));
   Ruthenium(methylbenzene)(methylglyoxal(bis-isopropylimine));
   Ruthenium(methylbenzene)(methylglyoxal(bis-nbutylimine));
   Ruthenium(methylbenzene)(methylglyoxal(bis-tertbutylimine));

Ruthenium(methylbenzene)(methylglyoxal(bis-isobutylimine));

Ruthenium(methylbenzene)(methylglyoxal(bis-trimethylsilylimine));

Ruthenium(methylbenzene)(methylglyoxal(bis-trifluoromethylimine));

Ruthenium(methylbenzene)(dimethylglyoxal(bis-methylimine));

Ruthenium(methylbenzene)(dimethylglyoxal(bis-ethylimine));

Ruthenium(methylbenzene)(dimethylglyoxal(bis-npropylimine));

Ruthenium(methylbenzene)(dimethylglyoxal(bis-isopropylimine));

Ruthenium(methylbenzene)(dimethylglyoxal(bis-nbutylimine));

Ruthenium(methylbenzene)(dimethylglyoxal(bis-tertbutylimine));

Ruthenium(methylbenzene)(dimethylglyoxal(bis-isobutylimine));

Ruthenium(methylbenzene)(dimethylglyoxal(bis-trimethylsilylimine)); and

Ruthenium(methylbenzene)(dimethylglyoxal(bis-trifluoromethylimine)).

3. The process of claim 1, wherein the ruthenium containing precursor is Ruthenium(benzene)(dimethylglyoxal(bis-isopropylimine)) or Ru(benzene)(glyoxalbis-isopropylimine).

4. The method of claim 1, wherein the ruthenium containing film is Ru.

5. The method of claim 1, further comprising annealing the ruthenium containing film.

6. The method of claim 1, further comprising maintaining the reactor at a temperature between about 25° C. to about 500° C. preferably between about 50° C. and about 350° C.

7. The method of claim 1, further comprising maintaining the reactor at a pressure between about 1 Pa and about $10^5$ Pa, preferably between about 10 Pa and about $10^3$ Pa.

8. The method of claim 1, further comprising introducing at least one reactant into the reactor.

9. The method of claim 8, wherein the ruthenium-containing precursor and the reactant are introduced into the chamber substantially simultaneously, and the chamber is configured for chemical vapor deposition.

10. The method of claim 9, wherein the chamber is configured for plasma enhanced chemical vapor deposition.

11. The method of claim 8, wherein the ruthenium-containing precursor and the reactant are introduced into the chamber sequentially, and the chamber is configured for atomic layer deposition.

12. The method of claim 11, wherein the chamber is configured for plasma enhanced atomic layer deposition.

13. The method of claim 11, wherein the chamber is configured for spatial atomic layer deposition.

14. The method of claim 9, wherein the reactant is selected from the group consisting of $H_2$, $NH_3$, $SiH_4$, $Si_2H_6$, $Si_3H_8$, $(CH_3)_2SiH_2$, $(C_2H_5)_2SiH_2$, $(CH_3)SiH_3$, $(C_2H_5)SiH_3$, phenyl silane, $N_2H_4$, $N(SiH_3)_3$, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$, $(CH_3)HNNH_2$, $(CH_3)_2NNH_2$, phenyl hydrazine, N-containing molecules, $B_2H_6$, 9-borabicyclo[3,3,1]nonane, dihydrobenzenfuran, pyrazoline, trimethylaluminium, dimethylzinc, diethylzinc, radical species thereof, and mixtures thereof.

15. The method of claim 9, wherein the reactant is selected from the group consisting of: $O_2$, $O_3$, $H_2O$, $H_2O_2$, oxygen containing radicals such as O— or OH—, NO, $NO_2$, carboxylic acids, formic acid, acetic acid, propionic acid, and mixtures thereof.

16. The method of claim 11, wherein the reactant is selected from the group consisting of $H_2$, $NH_3$, $SiH_4$, $Si_2H_6$, $Si_3H_8$, $(CH_3)_2SiH_2$, $(C_2H_5)_2SiH_2$, $(CH_3)SiH_3$, $(C_2H_5)SiH_3$, phenyl silane, $N_2H_4$, $N(SiH_3)_3$, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$, $(CH_3)HNNH_2$, $(CH_3)_2NNH_2$, phenyl hydrazine, N-containing molecules, $B_2H_6$, 9-borabicyclo[3,3,1]nonane, dihydrobenzenfuran, pyrazoline, trimethylaluminium, dimethylzinc, diethylzinc, radical species thereof, and mixtures thereof.

17. The method of claim 11, wherein the reactant is selected from the group consisting of: $O_2$, $O_3$, $H_2O$, $H_2O_2$, oxygen containing radicals such as O— or OH—, NO, $NO_2$, carboxylic acids, formic acid, acetic acid, propionic acid, and mixtures thereof.

18. The process of claim 1, wherein the ruthenium containing precursor is Ruthenium(benzene)(dimethylglyoxal(bis-isopropylimine)).

19. The process of claim 1, wherein the ruthenium containing precursor is Ru(benzene)(glyoxalbis-isopropylimine).

20. The process of claim 1, wherein the ruthenium containing precursor is Ruthenium(methylbenzene)(dimethylglyoxal(bis-isopropylimine)) or Ruthenium(methylbenzene)(glyoxal(bis-isopropylimine)).

* * * * *